United States Patent [19]

Dubief et al.

[11] Patent Number: 5,679,357
[45] Date of Patent: Oct. 21, 1997

[54] CATIONIC DISPERSIONS BASED ON CERAMIDES AND/OR GLYCOCERAMIDES

[75] Inventors: Claude Dubief, Le Chesnay; Danièle Cauwet, Paris, both of France

[73] Assignee: L'Oreal, Paris, France

[21] Appl. No.: 372,720

[22] Filed: Jan. 13, 1995

Related U.S. Application Data

[63] Continuation of Ser. No. 30,464, filed as PCT/FR92/00746, Jul. 30, 1992, abandoned.

[30] Foreign Application Priority Data

Aug. 1, 1991 [FR] France ................... 91 09824

[51] Int. Cl.⁶ .................. A61K 7/00; A61K 7/07
[52] U.S. Cl. ............. 424/401; 424/70.28; 424/47; 514/846; 514/847
[58] Field of Search .................. 424/401, 70.1, 424/70.28, 47; 514/846, 847

[56] References Cited

FOREIGN PATENT DOCUMENTS

| | | |
|---|---|---|
| 0 260 697 | 3/1988 | European Pat. Off. . |
| 0 278 505 | 8/1988 | European Pat. Off. . |
| 0 420 722 | 4/1991 | European Pat. Off. . |
| 0 446 094 | 9/1991 | European Pat. Off. . |
| 260008 | 11/1986 | Japan . |
| 120308 | 6/1987 | Japan . |
| 260508 | 6/1987 | Japan . |

*Primary Examiner*—Sallie M. Gardner
*Attorney, Agent, or Firm*—Jacobson, Price, Holman & Stern, PLLC

[57] ABSTRACT

Cationic dispersion containing at least 1) one natural or synthetic ceramide or glycoceramide or a mixture of natural or synthetic ceramides and/or glycoceramides of formula (I) where $R_1$ denotes $C_{14}$–$C_{30}$ alkyl, $R_2$ denotes hydrogen, (glycosyl)$_n$, (galactosyl)$_m$ or sulfogalactosyl, n having the value 1 to 4 and m having the value 1 to 8, $R_3$ denotes a $C_{15}$–$C_{26}$ hydrocarbon radical or a $C_{15}$–$C_{26}$ α-hydroxyalkyl radical in the case of the natural ceramides and/or glycoceramides; 2) a compound of formula (II) where X is an anion and a) $R_4$, $R_5$ and $R_6$ denote $C_1$–$C_4$ alkyl and $R_7$ denotes $C_{22}$ alkyl, or b) $R_4$ and $R_5$ denote $C_1$–$C_4$ alkyl and: (i) $R_6$ and $R_7$ denote $C_{20}$–$C_{22}$ alkyl; or (ii) $R_6$ denotes $C_{22}$ alkyl and $R_7$ denotes benzyl; or c) $R_4$ denotes $C_1$–$C_4$ alkyl, $R_5$ denotes (alkyl and/or alkenyl)amidoethyl and $R_6$ and $R_7$ denote 4,5-dihydroimidazole substituted in position 2 by a $C_{13}$–$C_{21}$ alkyl and/or alkenyl.

14 Claims, No Drawings

CATIONIC DISPERSIONS BASED ON CERAMIDES AND/OR GLYCOCERAMIDES

This application is a continuation of application Ser. No. 08/030,464, filed as PCT/FR92/00746 Jul. 30, 1992, now abandoned.

The present invention relates to catonic dispersions for treating the hair or the skin, to cosmetic compositions containing them and to their cosmetic applications.

It is well known that the hair is sensitized or weakened to various degrees by the action of atmospheric agents, and by the action of various hair treatments such as permanent waves, hair straightening, dyeing or bleaching. The hair then becomes difficult to disentangle and to style. Moreover, it becomes rough to the touch.

To facilitate disentangling and to improve its softness to the touch, cationic surface-active agents are commonly used. These surface-active agents unfortunately have a tendency to make the hair lank and to give it a greasy appearance. This phenomenon becomes more marked, the finer the hair that is treated.

Ceramides have already been proposed in hair compositions. Due to their insolubility in aqueous media, they have until now often been used in formulations based on anionic and/or nonionic surface-active agents.

The Applicant company has observed that emulsions or solutions based on ceramides did not make it possible to obtain good hair-disentangling properties.

The Applicant company has discovered, surprisingly, that by using aqueous dispersions based on ceramides and/or glycoceramides combined with specific cationic surface-active agents, the disentangling of hair was substantially improved without making the hair lank or greasy, while obtaining an even smoothing and sheathing from the root to the tip of the hairs.

The dispersions, according to the invention, also make it possible to reduce the wettability of the hair and thus to achieve faster drying.

The cationic dispersions according to the invention are particularly suitable for treating sensitized hair and fine hair. They are particularly stable.

The Applicant company has also observed that the cationic dispersions of the invention exhibited entirely satisfactory cosmetic properties with respect to the skin and could be applied for treating and caring for the skin.

The subject of the present invention is a cationic dispersion based on ceramides and/or glycoceramides combined with specific cationic surface-active agents.

Another subject relates to cosmetic compositions, containing these dispersions, for treating the hair or the skin.

A treatment having the effect of improving the esthetic appearance of the hair or the skin is called "cosmetic treatment".

Another subject relates to processes for cosmetic treatments using the compositions of the invention.

Other subjects of the invention will appear in the light of the description and examples which follow.

The cationic dispersions of the invention are characterized in that they contain in an aqueous medium:

1) at least one natural or synthetic ceramide or glycoceramide, or a mixture of natural or synthetic ceramides and/or glycoceramides of formula:

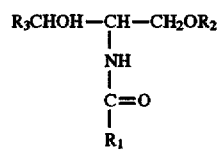

in which:

$R_1$ denotes a saturated or unsaturated, linear or branched alkyl radical derived from $C_{14}$–$C_{30}$ fatty acids, it being possible for the said radical to be substituted by a hydroxyl group in the α position or a hydroxyl group in the ω position esterified by a saturated or unsaturated, $C_{16}$–$C_{30}$ fatty acid;

$R_2$ denotes a hydrogen or a (glycosyl)$_n$, —(galactosyl)$_m$ or sulfogalactosyl radical, where n is an integer ranging from 1 to 4, and m is an integer ranging from 1 to 8;

$R_3$ denotes a $C_{15}$–$C_{26}$ hydrocarbon radical, saturated or unsaturated in the α position, which can be substituted by one or a number of $C_1$–$C_{14}$ alkyl radicals; in the case of natural ceramides or glyceramides [sic], $R_3$ can also denote a $C_{15}$–$C_{26}$ α-hydroxyalkyl radical, the hydroxyl group optionally being esterified by a $C_{16}$–$C_{30}$ α-hydroxy acid; and 2) at least one cationic surface-active agent of formula:

in which X denotes an anion and:

a) $R_4$, $R_5$ and $R_6$, which are identical or different, denote a $C_1$–$C_4$ alkyl radical; $R_7$ denotes a $C_{22}$ alkyl radical; or b) $R_4$ and $R_5$ are $C_1$–$C_4$ alkyl radicals, which are identical or different; and (i) $R_6$ and $R_7$ are $C_{10}$–$C_{22}$ alkyl radicals, which are identical or different, with the proviso that the total number of carbon atoms of $R_6$ and $R_7$ is greater than or equal to 20; it being possible for the alkyl radical to be interrupted by an ester group and/or an amido group; or (ii) the radical $R_7$ denotes a benzyl group and $R_6$ a $C_{22}$ alkyl radical; or c) $R_4$ denotes a $C_1$–$C_4$ alkyl radical;

$R_5$ denotes an (alkyl and/or alkenyl)amidoethyl radical, in which the alkyl and/or alkenyl radical is $C_{13}$–$C_{21}$;

$R_6$ and $R_7$ form, together with the nitrogen to which they are bonded, a 4,5-dihydroimidazole heterocycle substituted in position 2 by a $C_{13}$–$C_{21}$ alkyl and/or alkenyl radical.

In the formula (II) as defined above, the anion X preferably denotes chlorine or $CH_3OSO_3^-$, and $R_4$ preferably denotes methyl.

The ceramides and/or glycoceramides/cationic surface-active agents ratio by weight is preferably less than or equal to 2.

The ceramides and/or glycoceramides of formula (I) are used alone or as mixtures. They are prepared from natural extracts originating from pig skin, bovine brain, eggs, blood cells, plants and the like. They are described in the patents JA-86/260,008 and JA-87/120,308 and in the application EP-0,278,505.

Among the compounds of formula (I) as defined above, there are preferably used those for which:

$R_1$ denotes a saturated or unsaturated alkyl derived from a $C_{16}$–$C_{22}$ fatty acid;

$R_2$ denotes hydrogen;
$R_3$ denotes a saturated linear $C_{15}$ radical,
Such compounds are, for example:
N-linoleoyldihydrosphingosine
N-oleoyldihydrosphingosine
N-palmitoyldihydrosphingosine
N-stearoyldihydrosphingosine
N-behenoyldihydrosphingosine,
or mixtures of these compounds.

There are also preferably used those for which:
$R_1$ denotes a saturated or unsaturated alkyl radical derived from a fatty acid;
$R_2$ denotes galactosyl or sulfogalactosyl; and
$R_3$ denotes $—CH=CH—(CH_2)_{12}—CH_3$.

There may be mentioned the product consisting of a mixture of these compounds, sold under the commercial name Glycocer by the Company Waitaki International Biosciences.

The cationic surface-active agents of formula (II) of the invention are preferably chosen from the group formed by:

a) the tetraalkylammonium halides, such as behenyltrimethylammonium chloride or dimethyldistearylammonium chloride.

b) a quaternary ammonium salt of formula (III):

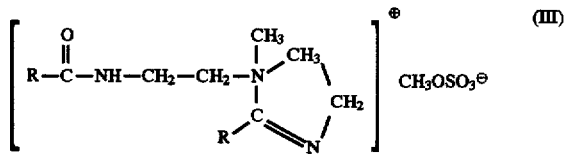

in which R denotes a mixture of $C_{13}$–$C_{21}$ alkenyl and/or alkyl radicals derived from tallow fatty acids, such as, for example, the products sold under the commercial name Rewoquat (W 75, W 75 PG, W 90, W 90 DPG, W 1599,W 75 H) by the Company Rewo.

c) stearamidopropyldimethyl(myristylacetate)ammonium chloride such as, for example, the product sold under the name Ceraphyl 70 by the Company Mallinckrodt.

The cationic dispersions in accordance with the invention can be prepared by forming a paste of the cationic surface-active agent and of the ceramide, followed by melting the mixture at a temperature of approximately 80° C. and then adding hot water (80°–90° C.) with vigorous stirring using an Ultraturrax.

In the dispersions according to the invention, the ceramide and/or glycoceramide compound of formula (I) is present in concentrations between 0.01 and 15% by weight, preferably between 0.05 and 10% by weight, with respect to the total weight of the dispersion and the cationic surface-active agent of formula (II) is present in concentrations of 0.01 to 15% by weight, and preferably of 0.05 to 10% by weight, with respect to the total weight of the dispersion.

The cationic dispersions according to the invention can be incorporated in cosmetic compositions for treating the hair or the skin, in order to be used in particular as shampoos, as rinsable products applied before or after shampooing, before or after dyeing or bleaching, before or after a permanent wave or hair straightening or between their two stages of reduction and oxidation; as non-rinsed hair care products, to be applied after a shampoo; as hair setting or blow drying lotions; as skin care compositions.

These cosmetic compositions then contain the ceramides and/or glycoceramides of formula (I) in proportions between 0.005 and 15% by weight, and preferably between 0.01 and 10%, with respect to the total weight of the composition and the cationic surface-active agent of formula (II) in proportions between 0.01 and 15% by weight, and preferably between 0.05 and 10% by weight, with respect to the total weight of the composition.

The cosmetic compositions according to the invention have a pH generally between 2 and 9 and more particularly between 3 and 7.

These compositions can be provided in the form of more or less thick liquids, of gels, of creams, of aerosol foams or of sprays.

The compositions can also contain, in addition to the dispersion defined above, viscosity regulating agents, such as electrolytes, hydrotropic agents or thickeners. Among these compounds, there may be especially mentioned: sodium chloride, sodium xylenesulfonate, the cellulose derivatives, such as for example carboxymethylcellulose and hydroxypropylcellulose, the xanthan gums, guar gum, hydroxypropylated guar gums and scleroglucans.

These viscosity regulating agents are used in proportions ranging up to 15% by weight with respect to the total weight of the composition and preferably below 6%.

The compositions in accordance with the invention can optionally additionally contain other agents having the effect of improving the cosmetic properties of the hair or the skin, provided that they do not detrimentally affect the stability of the compositions, such as anionic, nonionic or cationic polymers or quaternized or non-quaternized proteins and silicones.

The cationic, nonionic or anionic polymers, the quaternized or non-quaternized proteins and the silicones are used in the cosmetic compositions of the invention in proportions between 0.05 and 6%, and preferably between 0.1 and 3%, with respect to the total weight of the composition.

The compositions according to the invention can also contain various adjuvants usually used in cosmetics, such as fragrances, preserving agents, sequestering agents, foam stabilizing agents, propellants, dyes, acidifying or basifying agents and other adjuvants, depending upon the use envisaged.

Another subject of the invention consists of a process for cosmetic treatment of the hair or the skin comprising the application of a composition according to the invention, it being possible for this application to be optionally followed by a rinsing.

The examples which follow are used to illustrate the invention without, however, limiting it.

EXAMPLE 1

A dispersion having the following composition is prepared:

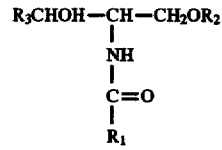

in which
$R_3=C_{15}H_{31}$
$R_1=C_{17}H_{33}$

| | |
|---|---|
| Dimethyldistearylammonium chloride | 2 g |
| Fragrance, preserving agent qs | |
| HCl qs pH = 4 | |
| Water qs | 100 g |

This cationic dispersion is applied to wet hair after a simple shampoo or a shampoo following upon a hair coloring. After rinsing with water, the wet hair is uniformly smooth and disentangles very evenly from the root to the tip.

After drying, it is smooth and light and the hair style has excellent form retention.

EXAMPLE 2

A dispersion having the following composition is prepared:

| | |
|---|---|
| Ceramide of Example 1 | 0.5 g |
| Behenyltrimethylammonium chloride containing 80% of AM | 2 g AM |
| Fragrance, preserving agent qs | |
| HCl qs     pH = 4 | |
| Water qs | 100 g |

This cationic dispersion is applied to the hair as in Example 1, the same results being obtained.

EXAMPLE 3

A dispersion having the following composition is prepared:

| | |
|---|---|
| Ceramide of Example 1 | 0.5 g |
| Quaternary ammonium salt of formula (II) sold under the name Rewoquat W 75 PG containing 75% of AM by the company Rewo | 2 g AM |
| Triethanolamine qs     pH = 6 | |
| Fragrance, preserving agent qs | |
| Water qs | 100 g |

This cationic dispersion is applied to hair which has been subjected to a reduction: 1st stage of a permanent wave. After rinsing, the oxidation stage of the permanent wave is carried out. The hair when wet and when dry exhibits the same advantages as those described in Example 1.

EXAMPLE 4

A dispersion having the following composition is prepared:

| | |
|---|---|
| Dimethyldistearylammonium chloride | 0.7 g |
| Ceramide of Example 1 | 1.4 g |
| Stearyl alcohol | 1.4 g |
| Cetyl alcohol | 1.4 g |
| Mixture of cetearyl alcohol and of cetearyl alcohol oxyethylenated by 33 moles of ethylene oxide | 3.6 g. |
| Triethanolamine qs     pH = 7 | |
| Water qs | 100 g |

This cationic dispersion is applied to wet hair which has been subjected to a permanent wave, that is to say after the oxidation stage. After rinsing with water, the hair when wet and when dry the same advantages as in Example 1.

EXAMPLE 5

A dispersion having the following composition is prepared:

| | |
|---|---|
| Ceramide of Example 1 | 2 g |
| Stearamidopropyldimethyl(myristylacetate)-ammonium chloride sold under the name Ceraphyl 70 by the company Mallinckrodt | 2 g |
| Spontaneous pH = 5 | |
| Water qs | 100 g |

This cationic dispersion is applied to hair which has been subjected to bleaching. After rinsing, the hair when wet and when dry exhibits the same advantages as in Example 1.

EXAMPLE 6

A dispersion having the following composition is prepared:

$$R_3CHOH-CH-CH_2OR_2$$
$$|$$
$$NH$$
$$|$$
$$C=O$$
$$|$$
$$R_1$$

in which $R_1=C_{21}H_{43}$ $R_3=C_{15}H_{31}$

| | |
|---|---|
| Dimethyldistearylammonium chloride | 5 g |
| Preserving agent qs | |
| Spontaneous pH = 5 | |
| Water qs | 100 g |

This cationic dispersion is applied to wet hair, after shampooing. Without rinsing the hair, it is dried and then styled. The hair is uniformly smooth, light, sheathed and easy to disentangle from the root to the tip.

EXAMPLE 7

A dispersion having the following composition is prepared:

| | |
|---|---|
| Glycoceramide containing 42% of AM, sold under the name Glycocer by the Company Waitaki International Biosciences | 0.1 g AM |
| Collagen hydrolysate quaternized by cocoylamidopropyldimethylamine, containing 30% of AM and sold under the name Lexein QX 3000 by the Company Aqualon | 0.3 g AM |
| Quaternary ammonium salt of formula (III), containing 75% of AM and sold under the name Rewoquat W 75 PG by the Company Rewo | 0.3 g AM |
| Hydroxyethylcellulose | 0.4 g |
| Preserving agent qs | |
| Spontaneous pH = 5 | |
| Water qs | 100 g |

This cationic dispersion is applied to washed and wet hair, optionally wound around rollers. Without rinsing the hair, it is dried. The hair exhibits the same advantages as in Example 6.

EXAMPLE 8

A dispersion having the following composition is prepared:

| | |
|---|---|
| Ceramide of Example 1 | 0.5 g |
| Dimethyldistearylammonium chloride | 5 g |
| Polydimethylsiloxane sold under the name Silbione oil 47 V 50 by the Company Rhône-Poulenc | 0.1 g |
| Preservative qs | |
| Spontaneous pH = 5 | |
| Water qs | 100 g |

This cationic dispersion is applied to clean, wet hair. After rinsing with water, the hair when wet and when dry exhibits the same advantages as in Example 1.

EXAMPLE 9

A dispersion of the following composition is prepared:

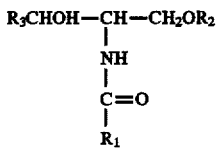

in which:
$R_1 = C_{21}H_{43}$
$R_3 = C_{15}H_{31}$

| | |
|---|---|
| Quaternary ammonium salt of formula (III), containing 75% of AM and sold under the name Rewoquat W 75 PG by the Company Rewo | 0.5 g AM |
| Preserving agent qs | |
| HCl qs    pH = 5 | |
| Water qs. | 100 g |

This cationic dispersion is applied to wet hair, after a shampoo. Without rinsing the hair, it is dried and then styled. The hair exhibits the same advantages as in Example 6.

EXAMPLE 10

A following composition for the bath or the shower is prepared:

| | |
|---|---|
| Glycoceramide containing 42% of AM, sold under the name Glycocer by the Company Waitaki International Biosciences | 0.2 g AM |
| Behenyltrimethylammonium chloride | 0.63 g |
| Sodium salt of sulfated oxyethylenated lauryl alcohol, sold under the name Empicol ESB/3FL by the Company Marchon | 30.0 g |
| Ether carboxylic acid polyoxyethylenated with 10 moles of ethylene oxide, sold under the name Akypo RLM 100 by the Company Chem Y, containing 90% of AM | 2.3 g AM |
| (Cocoylamidopropyl)hydroxypropylsulfo-betaine containing 50% of AM, sold under the name Amonyl 675 SB by the Company Seppic | 4.8 g AM |
| Fragrance qs | |
| Water qs | 100.0 g |

This shampoo for the bath or the shower has a very soft foam and imparts softness to the skin.

We claim:

1. Cationic dispersion for the treatment and care of the hair and the skin consisting essentially of in an aqueous medium:

1) at least one natural or synthetic ceramide or glycoceramide, or a mixture of natural or synthetic ceramides and/or glycoceramides of the following formula:

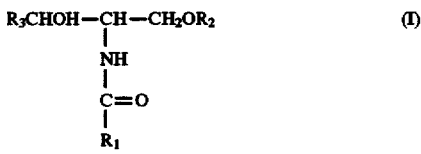

in which:

$R_1$ denotes a saturated or unsaturated, linear or branched alkyl radical derived from $C_{14}-C_{30}$ fatty acids optionally substituted by a hydroxyl group in the α position or a hydroxyl group in the ω position esterified by a saturated or unsaturated, $C_{16}-C_{30}$ fatty acid;

$R_2$ denotes a hydrogen or a (glycosyl)$_n$, —(galactosyl)$_m$ or sulfogalactosyl radical, where n is an integer ranging from 1 to 4, and m is an integer ranging from 1 to 8;

$R_3$ denotes a $C_{15}-C_{26}$ hydrocarbon radical, saturated or unsaturated in the α position, optionally substituted by one or more of $C_1-C_{14}$ alkyl radicals; in the case of natural ceramides or glycoceramide, $R_3$ can also denote a $C_{15}-C_{26}$ α-hydroxyalkyl radical, the hydroxyl group optionally being esterified by a $C_{16}-C_{30}$ α-hydroxy acid; and 2) at least one cationic surface-active agent of formula:

in which X denotes an anion and:

a) $R_4$, $R_5$ and $R_6$, which are identical or different, denote a $C_1-C_4$ alkyl radical; $R_7$ denotes a $C_{22}$ alkyl radical; or b) $R_4$ and $R_5$ are $C_1-C_4$ alkyl radicals, which are identical or different; and (i) $R_6$ and $R_7$ are $C_{10}-C_{22}$ alkyl radicals, which are identical or different, with the proviso that the total number of carbon atoms of $R_6$ and $R_7$ is greater than or equal to 20; the alkyl radical optionally being interrupted by an ester group and/or an amido group; or (ii) the radical $R_7$ denotes a benzyl group and $R_6$ a $C_{22}$ alkyl radical; or c) $R_4$ denotes a $C_1-C_4$ alkyl radical;

$R_5$ denotes an (alkyl and/or alkenyl)amidoethyl radical, in which the alkyl and/or alkenyl radical is $C_{13}-C_{21}$;

$R_6$ and $R_7$ form, together with the nitrogen to which they are bonded, a 4,5-dihydroimidazole heterocycle substituted in position 2 by a $C_{13}-C_{21}$ alkyl and/or alkenyl radical.

2. Dispersion according to claim 1, characterized in that the weight ratio of ceramide and/or glycoceramide of formula (I)/surface-active agent of formula (II) is less than or equal to 2.

3. Dispersion according to claim 1 characterized in that in the formula (II), X denotes chlorine or a $CH_3OSO_3^-$ group and $R_4$ denotes a methyl radical.

4. Dispersion according to claim 1, characterized in that the ceramide and/or glycoceramide compounds of formula (I) or their mixtures are selected from the group consisting of:

a) the compounds of formula (I) for which $R_1$ denotes a saturated or unsaturated alkyl radical derived from a $C_{16}-C_{22}$ fatty acid; $R_2$ denotes hydrogen; $R_3$ denotes a saturated linear $C_{15}$ hydrocarbon radical; and their mixtures;

b) the compounds of formula (I) for which $R_1$ denotes a saturated or unsaturated alkyl radical derived from a fatty acid; $R_2$ denotes galactosyl or sulfogalactosyl; and $R_3$ denotes the group —CH=CH—(CH$_2$)$_{12}$—CH$_3$; and their mixtures.

5. Dispersion according to claim 1, characterized in that the cationic surface-active agent, of formula (II), is chosen from the group formed by:

a) the tetraalkylammonium halides, selected from the group consisting of behenyltrimethylammonium chloride and dimethyldistearylammonium chloride;

b) a quaternary ammonium salt of formula:

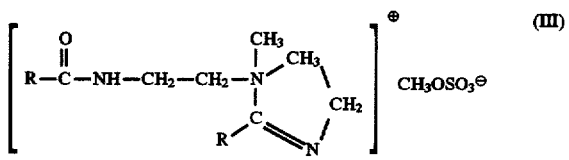

in which R denotes a mixture of $C_{13}$–$C_{21}$ alkenyl and/or alkyl radicals derived from tallow fatty acids, c) stearamidopropyldimethyl(myristylacetate)ammonium chloride.

6. Dispersion according to claim 1, characterized in that the compound of formula (I) is present in concentrations between 0.01 and 15% by weight with respect to the total weight of the dispersion and in that the cationic surface-active agent of formula (II) is present in concentrations between 0.01 and 15% by weight.

7. Cosmetic composition for treating the hair or the skin, characterized in that it contains, in a cosmetically acceptable aqueous vehicle, at least one dispersion defined according to claim 1.

8. Composition according to claim 7, characterized in that it contains the ceramide and/or glycoceramide compound of formula (I) in a concentration between 0.005 and 15% by weight and the cationic surface-active agent of formula (II) in concentrations between 0.01 and 15% by weight with respect to the total weight of the composition.

9. Composition according to claim 7, characterized in that it is provided in the form of liquids, of gels, of creams, of aerosol foams or of sprays.

10. Composition according to claim 7, characterized in that it additionally contains viscosity regulating agents in proportions ranging up to 15% by weight with respect to the total weight of the composition.

11. Composition according to claim 7, characterized in that it contains hair or skin conditioning agents chosen from anionic, nonionic or cationic polymers, quaternized or non-quaternized proteins or silicones in proportions between 0.05 and 6% by weight with respect to the total weight of the composition.

12. Composition according to claim 7, characterized in that it additionally contains fragrances, preserving agents, sequestering agents, foam stabilizing agents, propellants, dyes, acidifying or basifying agents or other cosmetic adjuvants.

13. Cosmetic composition according to claim 7, wherein said composition is a shampoo; a rinsable hair product to be applied before or after shampooing, before or after dyeing or bleaching, before or after a permanent wave or hair straightening or between their two states of reduction and oxidation; a non-rinsed hair care product to be applied after a shampoo, a hair setting or blow drying lotion; or a skin care product.

14. Process for the cosmetic treatment of the hair or the skin, characterized in that it comprises applying a composition according to claim 7 to the hair or the skin optionally followed by rinsing.

* * * * *